US00PP37124P2

(12) United States Plant Patent
Wang et al.

(10) Patent No.: US PP37,124 P2
(45) Date of Patent: Dec. 9, 2025

(54) APPLE TREE NAMED 'Farmer NO.4'

(50) Latin Name: *Malus sp.*
Varietal Denomination: Farmer NO.4

(71) Applicant: Zhejiang Yangshengtang Institute of Natural Medication Co., Ltd, Zhejiang (CN)

(72) Inventors: Hongxun Wang, Xinjiang (CN); Qiong He, Xinjiang (CN); Zhiqiang Bai, Xinjiang (CN); Xiaobo Cheng, Xinjiang (CN)

(73) Assignee: Zhejiang Yangshengtang Institute of Natural Medication Co., Ltd, Zhejiang (CN)

( * ) Notice: Subject to any disclaimer, the term of this patent is extended or adjusted under 35 U.S.C. 154(b) by 0 days.

(21) Appl. No.: 18/910,908

(22) Filed: Oct. 9, 2024

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

(56) References Cited

U.S. PATENT DOCUMENTS

PP29,960 P3 * 12/2018 Tupy ..... Plt./161

* cited by examiner

*Primary Examiner* — Karen M Redden
(74) *Attorney, Agent, or Firm* — Knobbe, Martens, Olson & Bear, LLP

(57) ABSTRACT

The new variety 'Farmer NO.4' is characterized by having brightly colored fruits with red flesh, high acidity, oblate shape, and rich soluble solids in the flesh.

8 Drawing Sheets

Latin name of the genus and species claimed: *Malus sp.* Variety denomination: 'Farmer NO.4'.

BACKGROUND AND SUMMARY OF THE NEW VARIETY

This application relates to the discovery and asexual propagation of a new and distinct variety of apple tree, *Malus* 'Farmer NO.4'. The new variety 'Farmer NO.4' was developed by collecting open-pollinated fruits of 'Hongxun No. 1' (unpatented) (Huocheng County, Yili area, Xinjiang, China). Seeds were obtained from the fruits and were sown to obtain seedlings. The new variety 'Farmer NO.4' was then selected by conducting seedling breeding, field primary selection, re-selection, internal content detection, and efficacy analysis by Hongxun Wang, Qiong He, Zhiqiang Bai, and Xiaobo Cheng. The new variety 'Farmer NO.4' was asexually reproduced in Huocheng County, Yili, Xinjiang, China, by grafting, using wild apple rootstock from Xinjiang, China, *Malus sieversii*, or common crabapple. The new variety, 'Farmer No.4', has been shown to maintain its distinct characteristics through succeeding asexual propagation.

The new variety 'Farmer NO.4' is characterized by having brightly colored fruits with red flesh, high acidity, oblate shape, and rich soluble solids in the flesh. Additionally, the fruit of the new variety 'Farmer NO.4' has higher levels of full-nutrition amino acids, organic acids, vitamins, and minerals compared to conventional fruits, along with high anthocyanin content, known for enhancing myocardial elasticity, lowering blood lipids, anti-thrombosis, inhibiting hypertension and arteriosclerosis, and protecting the liver and spleen.

The new variety 'Farmer NO.4' can be distinguished from 'Hongxun No. 1' (unpatented) in that the fruit of 'Farmer NO.4' has an oblate shape and deep coloration compared to round shape and medium coloration of 'Hongxun No. 1'.

The new variety 'Farmer NO.4' can be distinguished from 'Fuji' (U.S. Plant Pat. No. 7,001), 'Golden Delicious' (unpatented), and 'Gala' (U.S. Plant Pat. No. 4,121) by its smaller fruit size, purple-red flesh, high acidity and unsatisfactory fresh-eating flavor.

The detailed breeding process of 'Farmer NO.4' is described as follows:

In the fall of 2007, in Huocheng County, Yili area, Xinjiang, China, seeds were collected and sown to obtain live seedlings using 'Hongxun No. 1' as the parent tree, according to screening criteria of oblate shape of fruit, purple red color of flesh, absence of fruit ridge, strong resistance to diseases and pests, and strong cold resistance. Live seedlings from 'Hongxun No. 1' were screened from 2009 to 2018, and in 2019, 'Farmer NO.4' was finally obtained.

BRIEF DESCRIPTION OF THE DRAWINGS

The accompanying color photographic illustrations were taken in Qingshuihe Town, Huocheng County, Xinjiang during the growing seasons of the apple in 2021 and 2022 and the colors are as nearly true as is reasonably possible in a color representation of this type.

DETAILED BOTANICAL DESCRIPTION OF THE VARIETY

Figure 1:
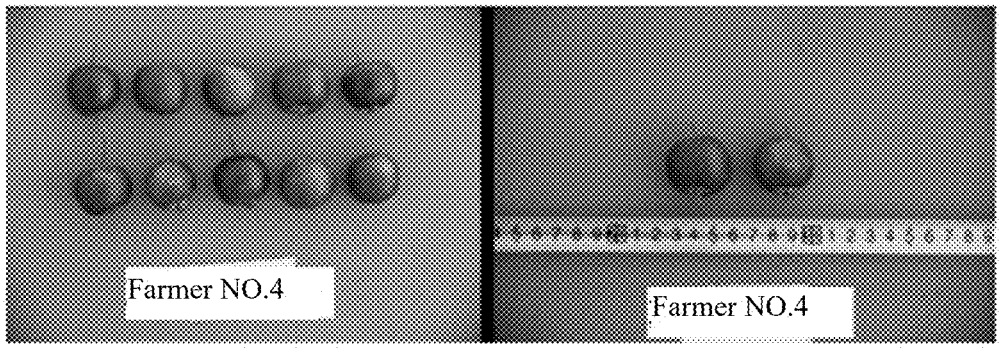
FIGS. 1A and 1B show the side view of the fruits of the new variety 'Farmer NO.4'.
Figure 2:
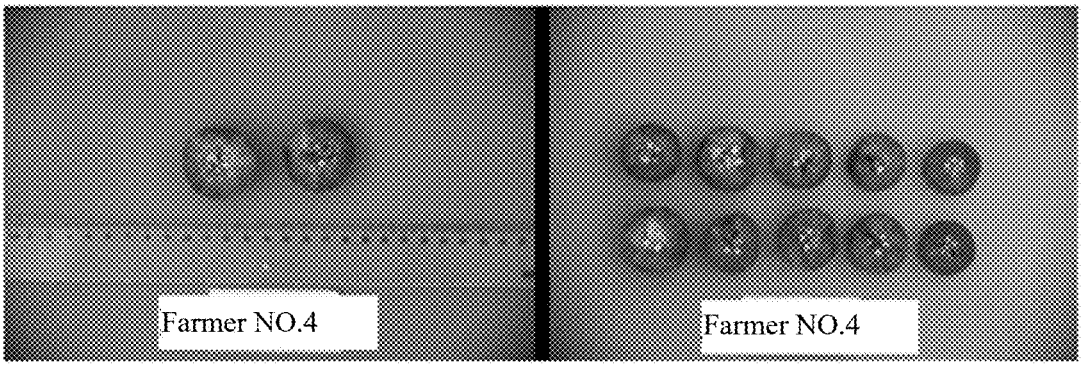
FIGS. 2A and 2B show the cross-section view of the fruits of the new variety 'Farmer NO.4'.
Figure 3:
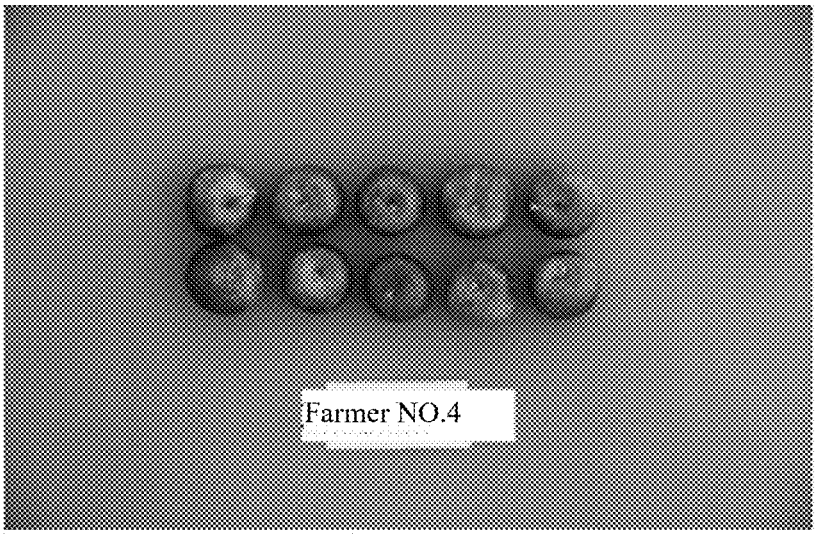
FIG. 3 shows the top view of the fruits of the new variety 'Farmer NO.4'.
Figure 4:
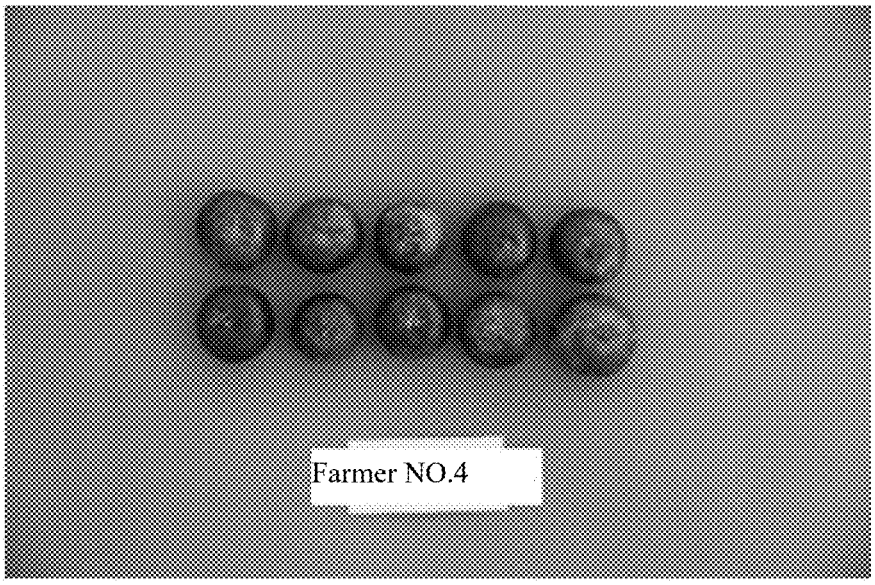
FIG. 4 shows the bottom view of the fruits of the new variety 'Farmer NO.4'.
Figure 5:
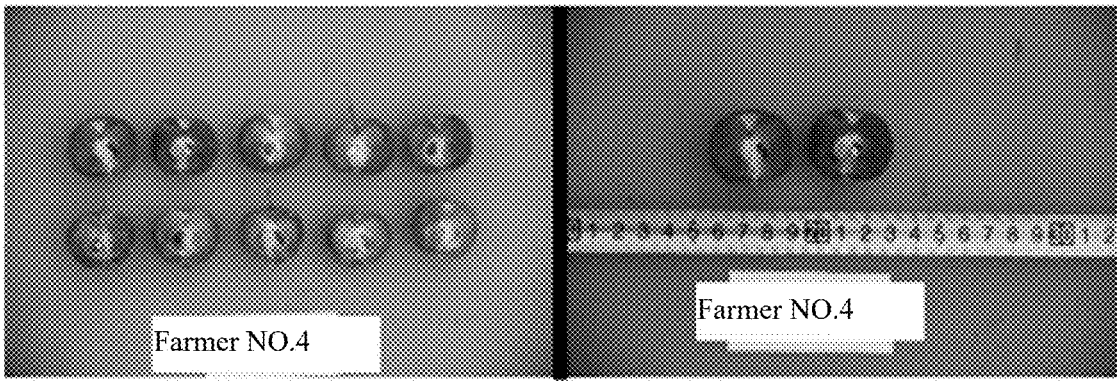
FIGS. 5A and 5B show the longitudinal section view of the fruits of the new variety 'Farmer NO.4'.
Figure 6:
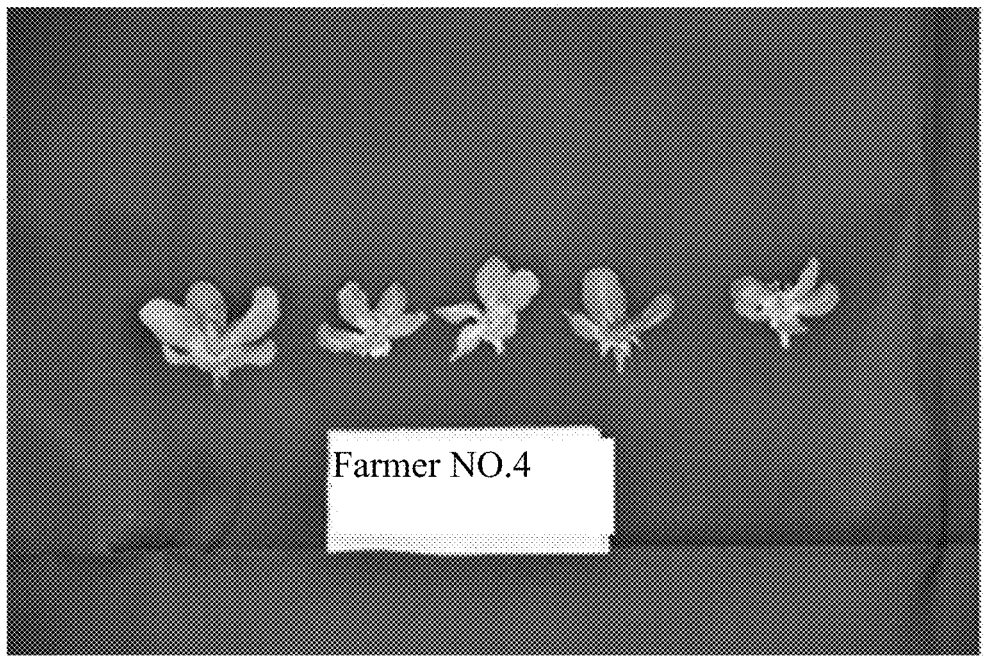
FIG. 6 shows the flowers of the new variety 'Farmer NO.4'.
Figure 7:
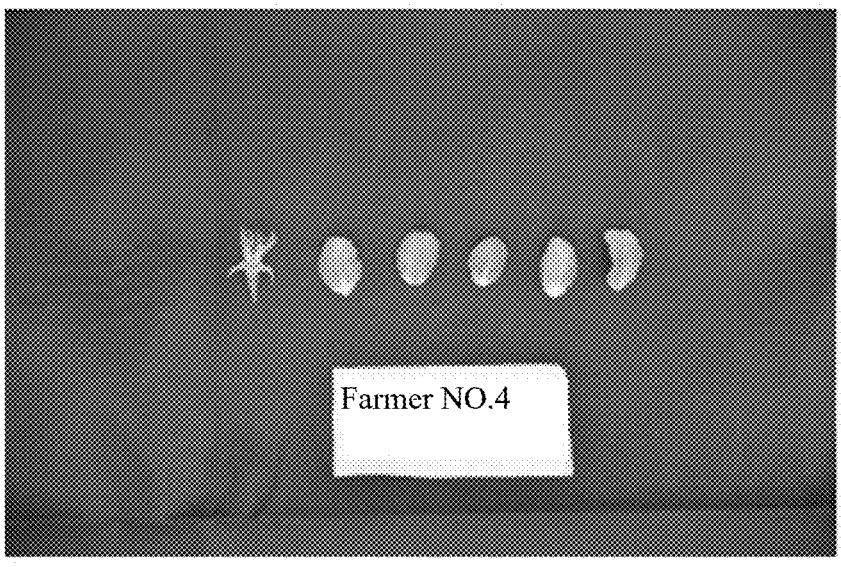
FIG. 7 shows the petals of the new variety 'Farmer NO.4'.
Figure 8:
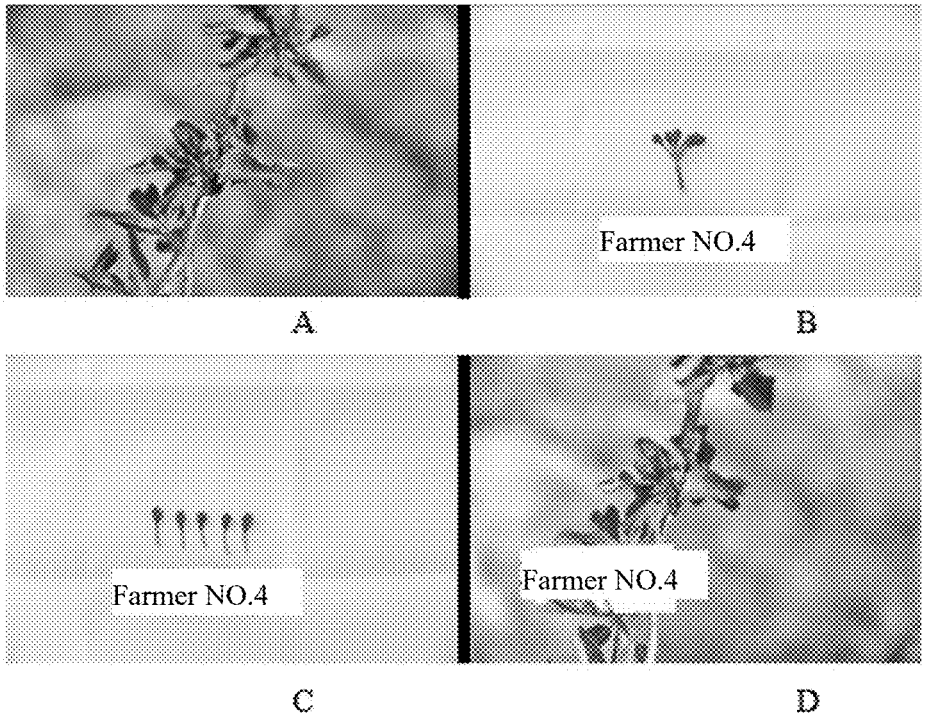
FIGS. 8A, 8B, 8C and 8D show the flower buds of the new variety 'Farmer NO.4'.
Figure 9:
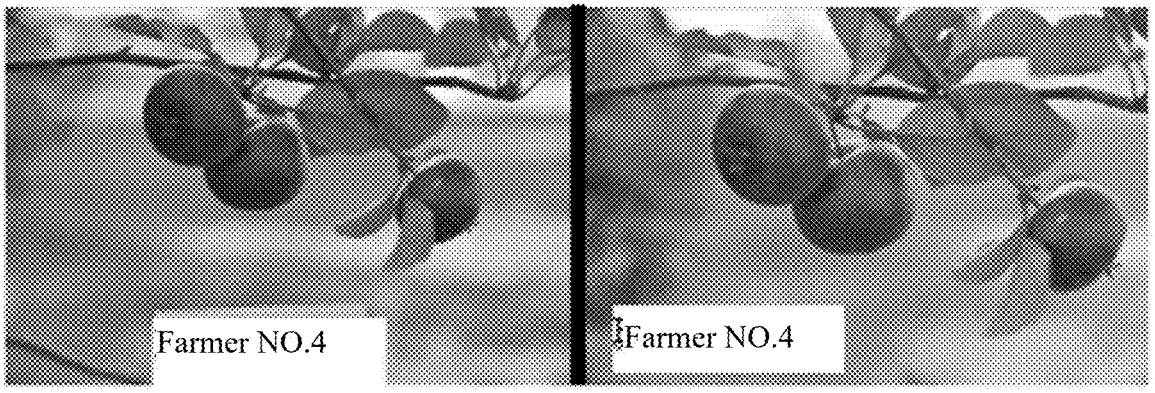
FIGS. 9A and 9B show the fruiting stage of the new variety 'Farmer NO.4'.
Figure 10:
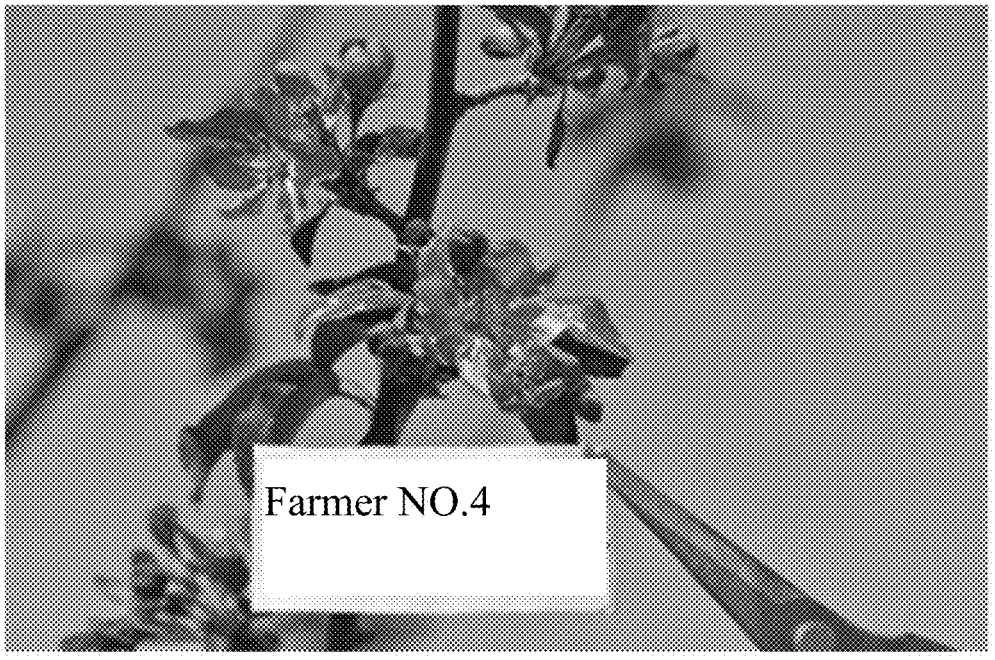
FIG. 10 shows the blooming stage of the new variety 'Farmer NO.4'.
Figure 11:
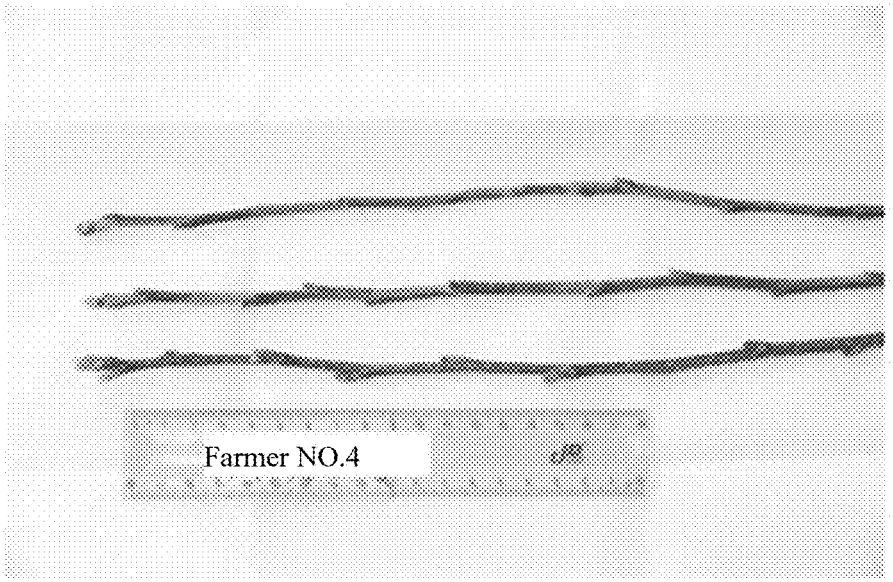
FIG. 11 shows the dormant branches of the new variety 'Farmer NO.4'.
Figure 12:
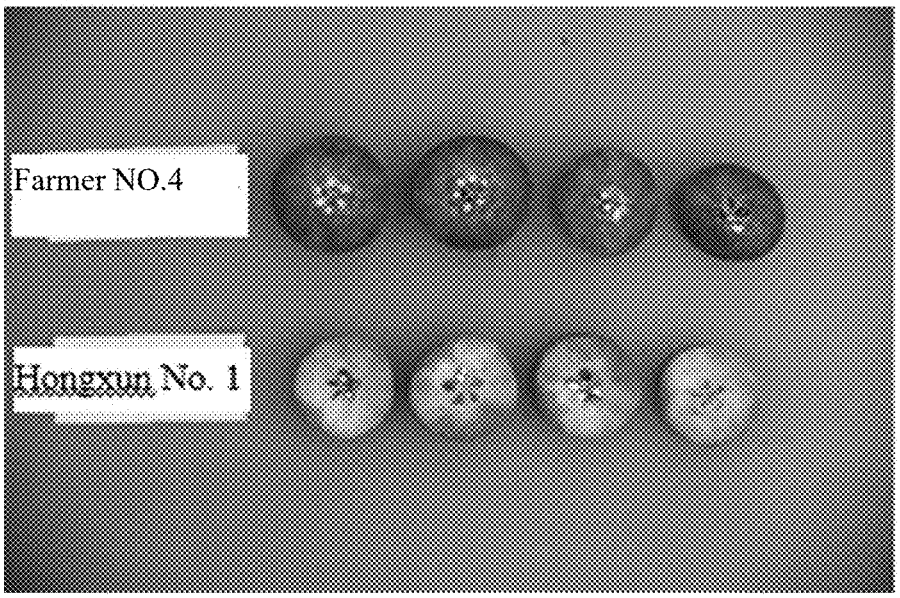
FIG. 12 shows the flesh of the new variety 'Farmer NO.4' compared to the flesh of 'Hongxun No. 1'.
Figure 13:
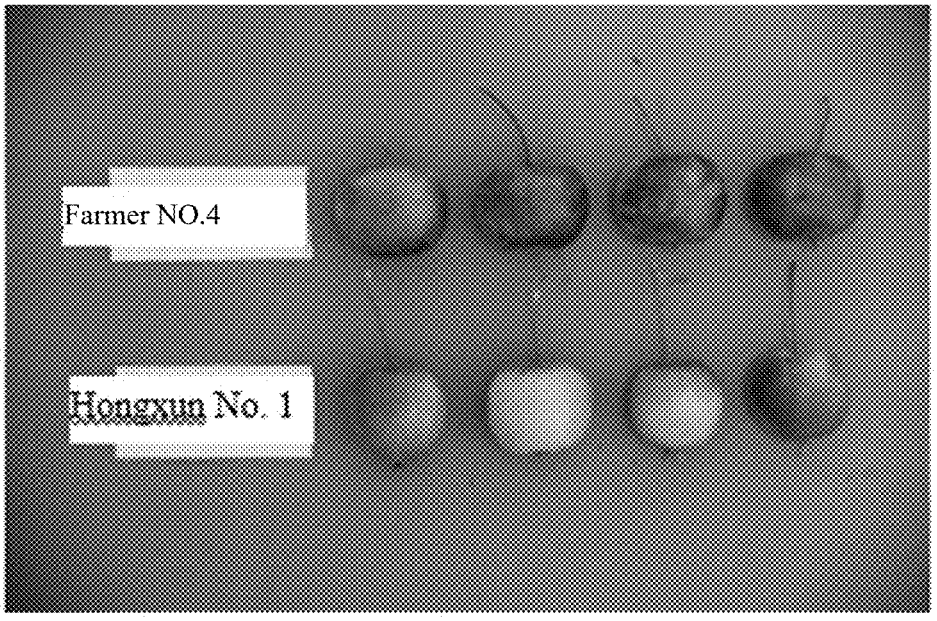
FIG. 13 shows the oblate-shaped fruits and deep coloration of the new variety 'Farmer NO.4' compared to the round-shaped fruits and medium coloration of 'Hongxun No.1'.
Figure 14:
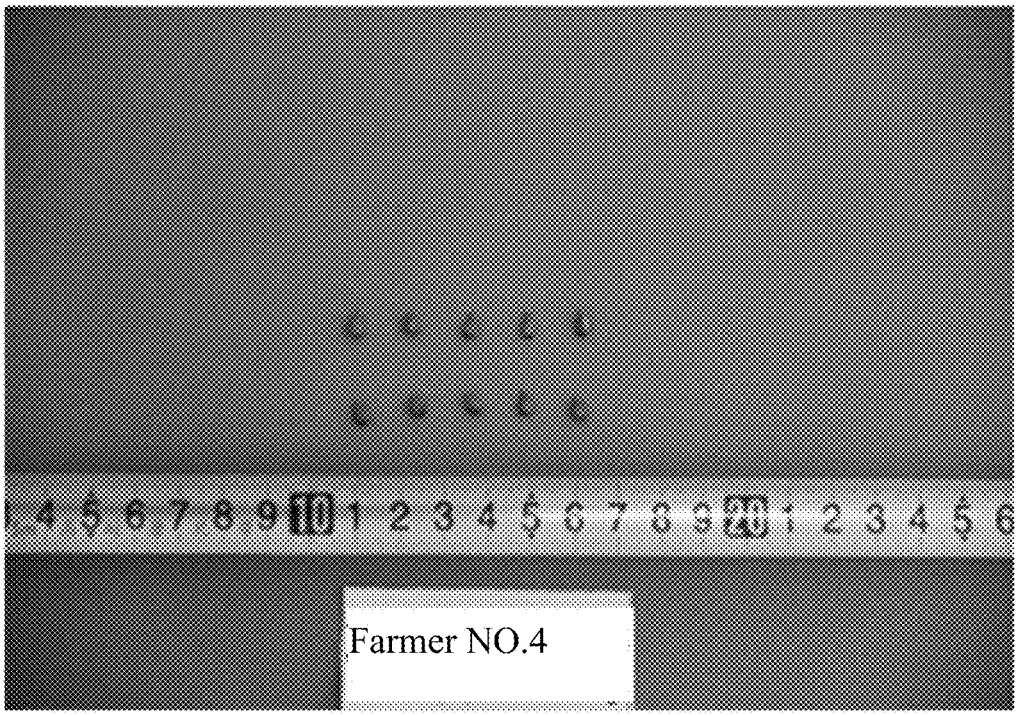
FIG. 14 shows the seeds of the new variety 'Farmer NO.4'.
Figure 15:
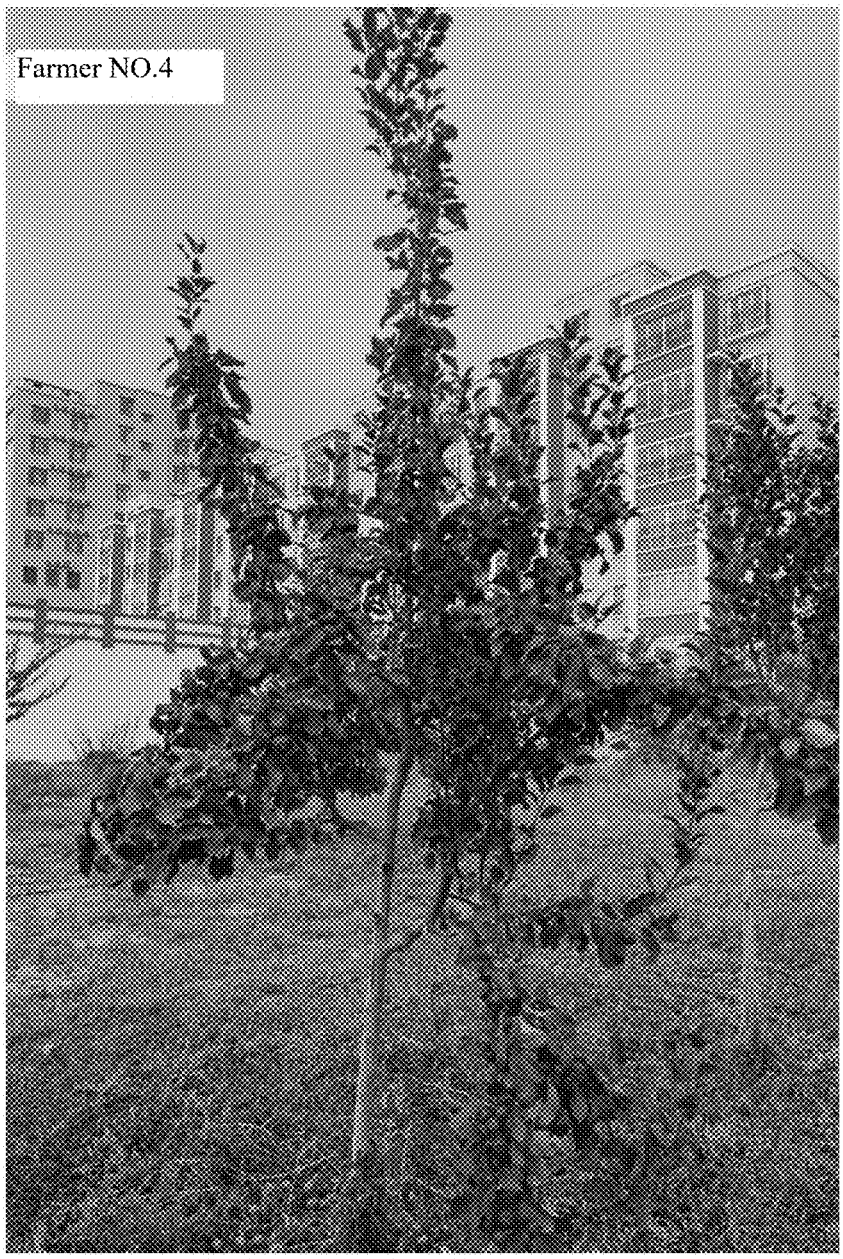
FIG. 15 shows the tree of the new variety 'Farmer NO.4'.

Throughout this specification, color names beginning with a small letter signify that the name of that color as used in common speech is aptly descriptive. Color names beginning with a capital letter designate values based upon the "CMYK International Standard Color Chart". Common color names are also occasionally used.

The descriptive matter which follows pertains to 5-year-old trees observed in the 7th Company of the 64th Regiment in Ili Prefecture, 'Farmer NO.4' grown in Qingshuihe Town, Huocheng County, Xinjiang, China, and it is believed to apply to trees of the same variety grown under similar conditions of soil and climate elsewhere. The characteristics of 'Farmer NO.4' trees and fruits were observed during the 2021 growing season and observations were continued in 2022. The observed characteristics may vary depending on location and season.

Tree:

General: (Measurements taken on a five-year-old tree unless otherwise noted).

*Vigor*.—Strong.
*Posture*.—Open.
*Form*.—Branched.

One year old branch: (Data taken in February).

*Pubescence density*.—Medium.
*Thickness*.—Very thin, approximately 0.6 cm.
*Length of internode*.—Small, approximately 3.77 cm.
*Number of lenticels*.—About 2 to 3 per $cm^2$.
*Height*.—Approximately 3 m to 4 m. Spread: Approximately 2 m. Diameter at Breast Height: Approximately 2.4 cm.

Foliage:

Spring shoot stop growth stage: (Data taken in June to July).

*Leaf posture*.—Up-right.
*Leaf blade length*.—Medium, approximately 11.2 cm.
*Leaf blade width*.—Narrow to medium, approximately 4.71 cm.
*Leaf blade length/width ratio*.—Very small, approximately 1.64.
*Leaf blade margin*.—Obtuse.
*Leaf blade length of petiole*.—Short, approximately 3.57 cm.
*Upper leaf blade color*.—About Dark Green C80M50Y60K40.
*Lower leaf blade color*.—About Brown Red C30M70Y60K40.
*Leaf blade flatness of leaf surface*.—Wavy.

Flowers:

*Flower buds color*.—About Purple Red C30M100Y90K20.
*Diameter of corolla*.—Small, approximately 3.99 cm.
*Relative position of petals*.—Discrete.
*Fragrance*.—Present.
*Average number of flowers per panicle*.—About 5 to 6.
*Diameter*.—Approximately 3.88 cm.
*Bud burst*.—About April $9^{th}$. Initial Bloom: Early, about April $11^{th}$. Full Bloom Period: About 7-10 days.
*Style color*.—About Light Purple C20M60Y0K10.
*Style length*.—Approximately 11.82 mm.
*Stigma color*.—About pink purple.
*Stigma diameter*.—Approximately 0.2 mm.
*Ovary color*.—About Light Purple C20M60Y0K10.
*Ovary length*.—Approximately 3.48 mm.

Sepals:

*Shape*.—Pointed.
*Number*.—About 5 per flower.
*Edge*.—Smooth.
*Color*.—About Wine Red C16M90Y60K60.
*Texture*.—Densely covered with short downy hairs.

Petals:

*Length*.—Approximately 19.88 mm.
*Width*.—Approximately 11.95 mm.
*Shape*.—Oblong.
*Apex shape*.—Hemispherical.
*Base shape*.—Tapered.
*Margin*.—Smooth.
*Veins*.—Raised.
*Color*.—About Purple Red C0M70Y0K40.
*Texture*.—Smooth with sparse short downy hairs.

Pedicle:

*Color*.—About Gray Green C0M40Y60K60.
*Length*.—Approximately 18.72 mm.
*Diameter*.—Approximately 1.02 mm.

Fruit:

*Edible maturation stage*.—Medium, about Mid to Late August.
*Single fruit weight*.—Very light, approximately 19.58 g.
*Fruit longitudinal diameter*.—Short, approximately 3.46 cm.
*Fruit*.—Transverse diameter — Small to medium, approximately 4.42 cm.
*Shape index*.—Very small, approximately 0.79.
*Widest part*.—Middle.
*Shape*.—Oblate.
*Fruit surface ridge*.—Absent or weak.
*Fruit apex ridge*.—Absent or weak.
*Closure state of sepal*.—Closed.
*Size of calyx*.—Small.

*Length of sepal*.—Long.
*Depth of calyx cavity*.—Shallow.
*Width of calyx cavity*.—Narrow.
*Calyx tube*.—Absent.
*Thickness of peduncle*.—Thin, approximately 1.2 mm.
*Length of peduncle*.—Very short to short, approximately 2.72 cm.
*Depth of peduncle cavity*.—Shallow.
*Width of peduncle cavity*.—Narrow.
*Fruit powder*.—Absent or few.
*Wax*.—Absent or few.
*Fruit base color*.—Light yellow.
*Area of coloration*.—Large.
*Cover color*.—About Purple Red C0M90Y5K80.
*Intensity of coloration*.—Medium.
*Pattern of coloration*.—Patchy.
*Stripe width over base color*.—Medium.
*Amount of rust on calyx cavity*.—Absent or few.
*Amount of rust on body of fruit*.—Few.
*Amount of rust on peduncle cavity*.—Absent or few.
*Diameter of dots*.—Small, less than 0.1 mm.
*Density of dots*.—Sparse.
*Texture of flesh*.—Crispy and Hard.
*Hardiness of flesh*.—Very hard, approximately 11.84 $kg/cm^2$.
*Juiciness*.—Medium.
*Soluble solids content*.—Medium, approximately 11.96%. Color of Flesh: About Red C0M90Y50K40. Size of Core: Medium, approximately 40.33%. Ventricular Condition: Closed. Self-fertility: Poor. Titratable Acidity Content: High, about 1.172266%. Number of Seeds: Medium, approximately 7.4.

Fruit use: Market Use (fresh-eating, processing, and ornamental).

Productivity: Approximate yield of 3 to 4 tons per acre (equivalent to approximately 836.67 to 1115.56 bushels per acre).

Disease resistance: The new variety 'Farmer NO.4' has strong disease resistance. No significant pests or diseases have been observed.

Cold tolerance: the new variety has strong cold tolerance, capable of withstanding a minimum temperature of −35° C. It is suitable for planting in areas south of 44° N latitude.

What is claimed is:

1. A new and distinct variety of apple tree named 'Farmer NO.4' as herein described and illustrated.

* * * * *

A B

A B

A B

A B